(12) United States Patent
Wimberley et al.

(10) Patent No.: US 9,549,822 B2
(45) Date of Patent: Jan. 24, 2017

(54) VERTEBRAL BODY REPLACEMENT OR FUSION DEVICE

(71) Applicant: DePuy Synthes Products, Inc., Raynham, MA (US)

(72) Inventors: David Wimberley, Houston, TX (US); Christopher Cain, Aurora, CO (US); Andreas Gfeller, Oberdorf (CH); Jared Schoenly, West Chester, PA (US); Frank Yohe, West Chester, PA (US); David Evans, West Chester, PA (US); Dirk Dittmann, Oberdorf (CH); Jayr Bass, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 439 days.

(21) Appl. No.: 13/886,900

(22) Filed: May 3, 2013

(65) Prior Publication Data
US 2014/0330383 A1  Nov. 6, 2014

(51) Int. Cl.
*A61F 2/44* (2006.01)
*A61F 2/30* (2006.01)
*A61F 2/46* (2006.01)

(52) U.S. Cl.
CPC ......... *A61F 2/4465* (2013.01); *A61F 2/30744* (2013.01); *A61F 2/4455* (2013.01);
(Continued)

(58) Field of Classification Search
CPC ............ A61F 2/4455; A61F 2002/4475; A61F 2/4611; A61F 2/4465; A61F 2/4464
(Continued)

(56) References Cited

U.S. PATENT DOCUMENTS 5,192,327 A    3/1993  Brantigan
6,143,033 A   11/2000  Paul et al.
(Continued)

FOREIGN PATENT DOCUMENTS

WO    2004/043291       5/2004
WO    2005097004 A2    10/2005
WO    2011/129973      10/2011

OTHER PUBLICATIONS

Bono, Christopher M., "Interspinous Spacers in the Lumbar Spine," US Musculoskeletal Review, 2007, pp. 44-46.
(Continued)

*Primary Examiner* — Christopher Beccia
(74) *Attorney, Agent, or Firm* — Meunier Carlin & Curfman LLC

(57) ABSTRACT

The present disclosure relates to a spinal implant or spacer that addresses the variation in anatomy of vertebrae along the spine by having inferior and superior surface angle and convexity variations that are adapted to address the differences in lordosis and endplate surface convexity of the spine. The difference between the convexity of the superior and inferior surface of the spacer increases as the lordotic angle of the spacer increases. The spacers described herein thus provide overall improved fit into vertebral disc space and in some embodiments are even used in the absence of fusion for a prolonged period. The vertebral spacers described herein in some embodiments are used with supplemental internal fixation systems, such as an anchor plate. The interior of the spacer has channels and undercuts to increase graft volume and retention, support bony ingrowth, and bony stability for better secondary and tertiary stabilization.

35 Claims, 7 Drawing Sheets

(52) U.S. Cl.
CPC ..... *A61F 2/4611* (2013.01); *A61F 2002/3008* (2013.01); *A61F 2002/30143* (2013.01); *A61F 2002/30176* (2013.01); *A61F 2002/30266* (2013.01); *A61F 2002/30324* (2013.01); *A61F 2002/30326* (2013.01); *A61F 2002/30487* (2013.01); *A61F 2002/30616* (2013.01); *A61F 2002/30772* (2013.01); *A61F 2002/30785* (2013.01); *A61F 2002/30828* (2013.01); *A61F 2002/30836* (2013.01); *A61F 2002/4475* (2013.01); *A61F 2310/00023* (2013.01); *A61F 2310/00179* (2013.01); *A61F 2310/00796* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 7,300,465 | B2 | 11/2007 | Paul et al. |
| 8,641,766 | B2 | 2/2014 | Donner et al. |
| 2004/0082999 | A1* | 4/2004 | Mathys, Jr. ........... A61F 2/4455 623/17.11 |
| 2006/0085071 | A1* | 4/2006 | Lechmann et al. ........ 623/17.11 |
| 2006/0100705 | A1* | 5/2006 | Puno ................... A61F 2/30771 623/17.11 |
| 2006/0217806 | A1 | 9/2006 | Peterman et al. |
| 2006/0235527 | A1 | 10/2006 | Buettner-Janz et al. |
| 2009/0062917 | A1 | 3/2009 | Foley et al. |
| 2011/0035007 | A1* | 2/2011 | Patel ..................... A61F 2/4465 623/17.11 |
| 2012/0078370 | A1 | 3/2012 | James et al. |
| 2012/0158143 | A1* | 6/2012 | Shapiro ................ A61F 2/4455 623/17.16 |
| 2012/0303128 | A1* | 11/2012 | Ullrich, Jr. ............. A61F 2/442 623/17.16 |
| 2013/0085573 | A1 | 4/2013 | Lemoine et al. |

OTHER PUBLICATIONS

Synthes® SynCage-LR/SynCage PROmotive, Implant and instrument system for anterior lumbar interbody fusion, Technique Guide, Apr. 2010, 40 pages.

Synthes® SynFix-LR, Implant and instrumentation for stand alone anterior lumbar interbody fusion (ALIF), Technique Guide, 2006, 26 pages.

International Search Report dated Oct. 22, 2014 from corresponding PCT Application No. PCT/US2014/035779 filed Apr. 29, 2014, 7 pages.

Machine translation of DE202011000202 dated Apr. 28, 2011 in the name of Aesculap AG.

* cited by examiner

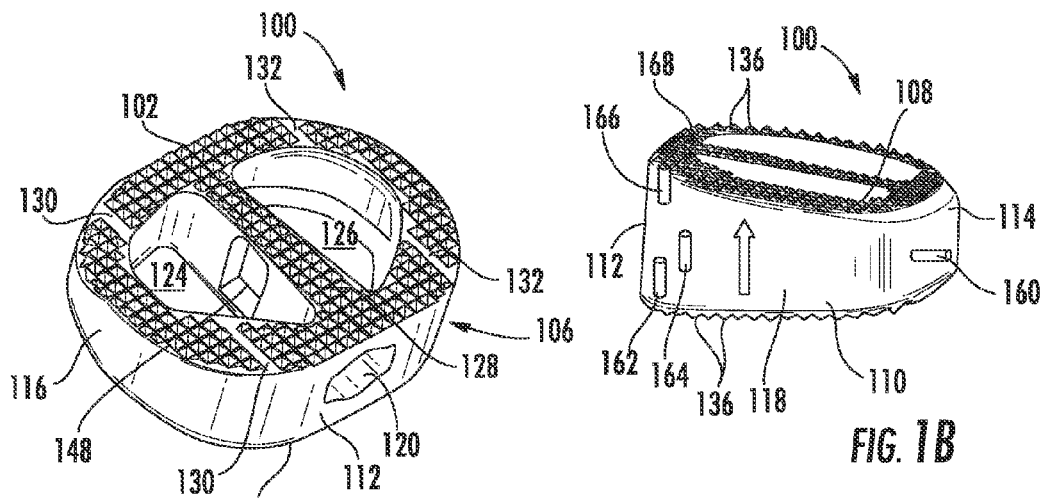
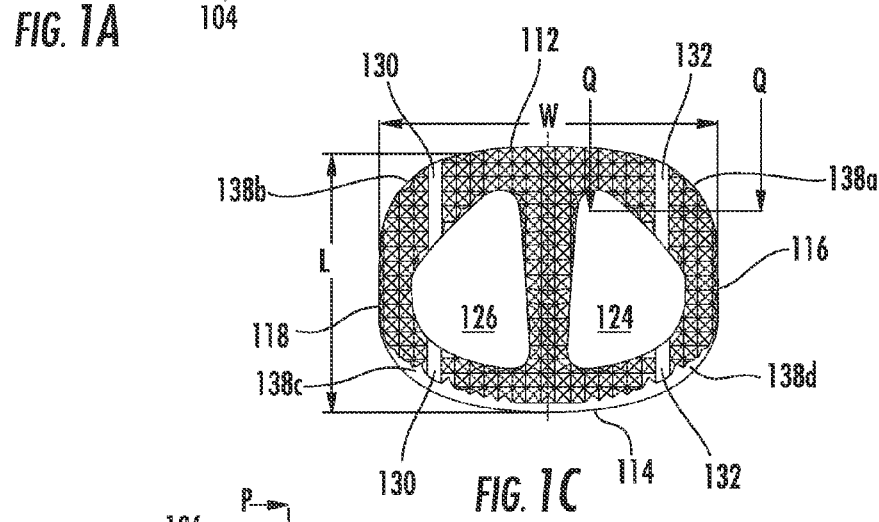
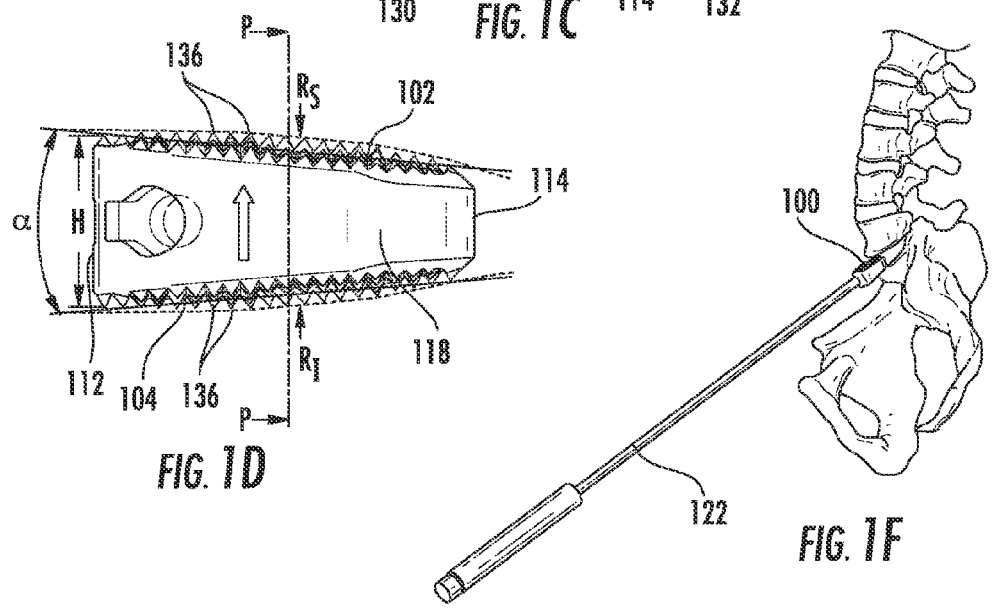

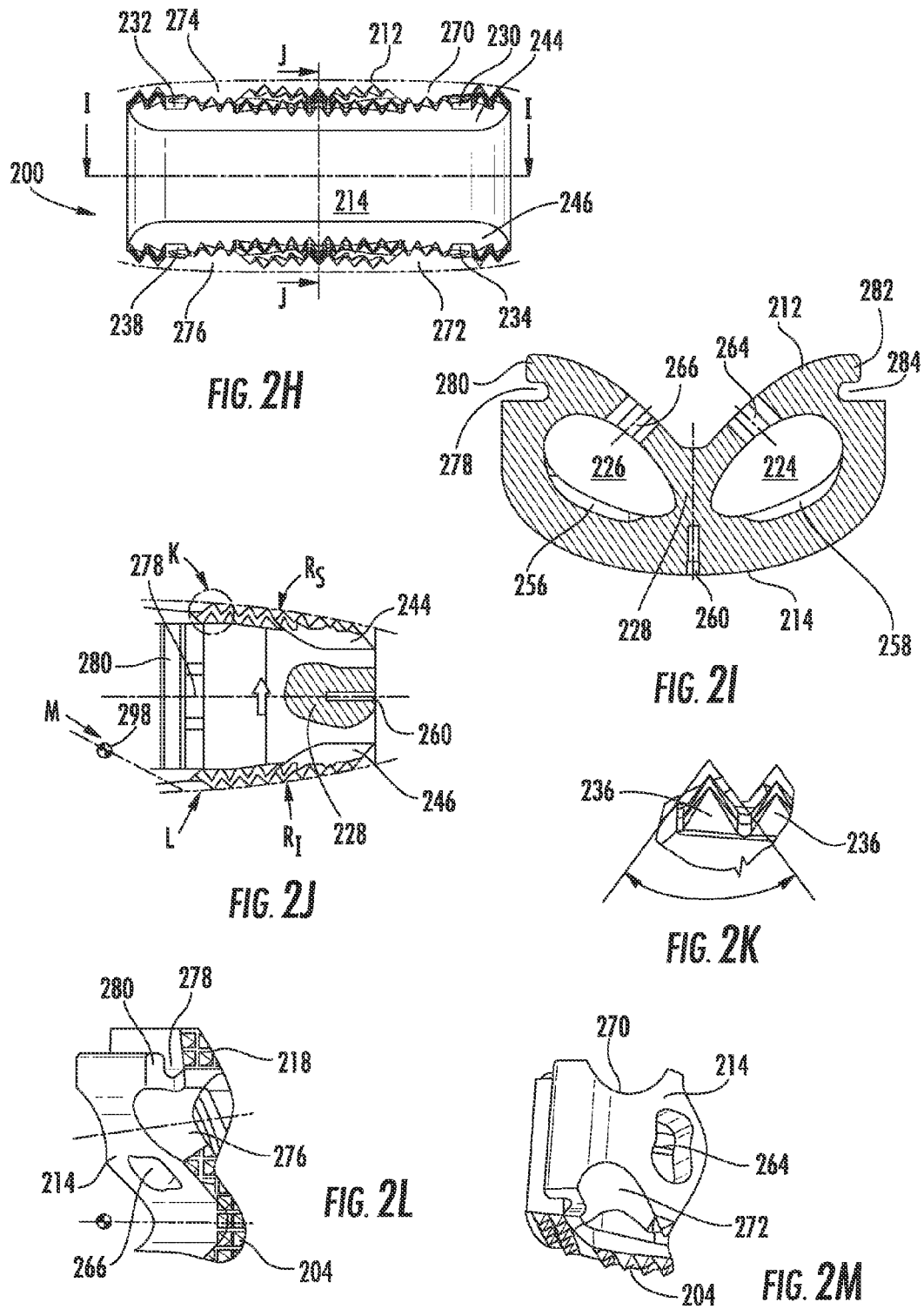

VERTEBRAL BODY REPLACEMENT OR FUSION DEVICE

TECHNICAL FIELD

The device disclosed herein relates generally to surgical implants for vertebral body replacement or fusion. Method of using the device in the thoraco lumbar spine to replace a collapsed, damaged, or unstable vertebral body is also discussed.

BACKGROUND

Spinal disc and/or vertebral bodies may be displaced, unstable, or damaged due to trauma (e.g. fracture), disease (e.g. tumor), degenerative effects, or wear over an extended period of time. The displacement, instability, or damage of the spinal disc and/or vertebral bodies often causes chronic back pain. In order to alleviate the chronic back pain, all or at least part of the problematic spinal disc is removed, optionally along with all or part of at least one of the neighboring vertebrae. The removal of the spinal disc and/or vertebral body leaves a void that is subsequently filled by insertion of a surgical implant or spacer into the void. The inserted surgical implant or spacer provides distraction of neighboring vertebral bodies and promotes the healing fusion of the remaining bony anatomy. The success of alleviation of the chronic pain is limited however, due to several factors. For example, the spacer or implant or cage used to fill the space left by the removed disc may not be strong enough to support the spine. The spacer may not remain in the position in which it is placed by the surgeon. The spacer may not comprise of such a material to promote bony growth around the spacer and within the spinal region. At least some of the limitations are due to the fact that the surgical implant or spacer failed to adequately address the variation in anatomy of the vertebrae along the spine.

SUMMARY

The present disclosure relates to spinal implants. For example, the spinal implants may be used for insertion into the intervertebral disc space. The spinal implants may be used for alleviating chronic back pain and promoting bony growth around the spinal implants. The spinal implants may also be positioned between two vertebral bodies and secured with at fixation elements.

In accordance with an aspect of the disclosure, there is provided a spinal implant for insertion between adjacent upper and lower vertebral endplates. The spinal implant may include superior and inferior surfaces for contacting the upper and lower endplates respectively with each surface comprising a plurality of surface teeth; and a side wall connecting the superior and inferior surfaces, wherein the side wall comprises an anterior wall and a posterior wall that are connected by a right lateral wall and a left lateral wall, wherein the posterior wall is shorter than the anterior wall such that an angulation between the superior and the inferior surfaces is from about 2 to about 30 degrees. At least one recess may be formed in the anterior wall, the recess being adapted to receive an insertion tool. Vertical through-channels may be provided that extend through the implant from the superior surface to the inferior surface with at least one vertical strut separating the channels.

A width of the implant is defined as a longitudinal distance between the centers of the right and left lateral walls, a length of the implant is defined as a horizontal distance between the centers of the anterior and posterior walls, and a height of the implant is defined as a vertical distance between the superior and inferior surfaces at an anterior most edge of the implant, the height accounting for a convexity of the superior and inferior surfaces and including one-half of a height of the surface teeth disposed on the superior and inferior surfaces. The superior and inferior surfaces are convex having respective radius of curvature values that diverge as the angulation between the superior and the inferior surfaces increases.

In accordance with another aspect of the disclosure, there is provide a spinal implant or spacer for insertion between adjacent upper and lower vertebral endplates. The spinal implant or spacer includes a spacer body comprising superior and inferior surfaces for contacting the upper and lower endplates respectively, the spacer body defining vertical through-channels extending through the spacer body from the superior surface to the inferior surface, wherein the superior and inferior surfaces are convex in shape and include a plurality of surface teeth. A side wall is provided to connect the superior and inferior surfaces, wherein the side wall comprises a posterior wall connected to a right lateral wall and a left lateral wall, wherein the lateral walls are connected to top open ends of a "V" shaped anterior wall with a bottom tip of the "V" connected to the posterior wall in the form of a vertical strut separating the through-channels, wherein the posterior wall is shorter than the anterior wall such that an angulation between the superior and the inferior surfaces is from about 2 to about 30 degrees. The spacer body may include two vertical recesses along the lateral walls approximate the connections between the posterior wall and the lateral walls to mate with inward pointing projections of an anchor plate.

In accordance with another aspect of the disclosure, there is provide a spinal implant that includes a body having a side wall, a superior surface, and an inferior surface, wherein the side wall comprises an anterior wall and a posterior wall that are connected by a right lateral wall and a left lateral wall, wherein the posterior wall is shorter than the anterior wall such that an angulation between the superior and the inferior surfaces is from about 2 to about 30 degrees. A vertical strut may extend from an interior surface of the right lateral wall to an interior surface of the left lateral wall forming a plurality of vertical through-channels within the body, the vertical through-channels further comprising undercuts that extend inwardly proximate to the inferior surface within the through-channels. At least one recess may be formed in the anterior wall, the recess being adapted to receive an insertion tool. The superior and inferior surfaces may be convex having respective radius of curvature values that diverge as the angulation between the superior and the inferior surfaces increases.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

In the drawings, like reference numbers and designations in the various drawings indicate like elements.

FIG. 1A is a schematic diagram of a left front perspective view of an embodiment of the vertebral spacer.

FIG. 1B is a schematic diagram of a right back side perspective view of the vertebral spacer of FIG. 1A.

FIG. 1C is a schematic diagram of a top view of the spacer of FIG. 1A.

FIG. 1D is a schematic diagram of a right side or left lateral view of the vertebral spacer of FIG. 1A.

FIG. 1F is a schematic diagram of the vertebral spacer of FIG. 1A being inserted between vertebral bodies of lumbar spine with an insertion tool.

FIG. 2H is a schematic diagram of a back view showing the posterior wall of the spacer of FIG. 2A.

FIG. 2I is a schematic diagram of a horizontal cross sectional view of the vertebral spacer of FIG. 2A along the line I-I of FIG. 2H.

FIG. 2J is a schematic diagram of a vertical cross sectional view of the vertebral spacer of FIG. 2A along the line J-J-I of FIG. 2H.

FIG. 2K is an enlarged view of the circled portion K of FIG. 2J.

FIG. 2L is a perspective view of the spacer along the arrow L of FIG. 2J.

FIG. 2M is a perspective view of the spacer along the arrow M of FIG. 2J.

DETAILED DESCRIPTION

Figure 1E:
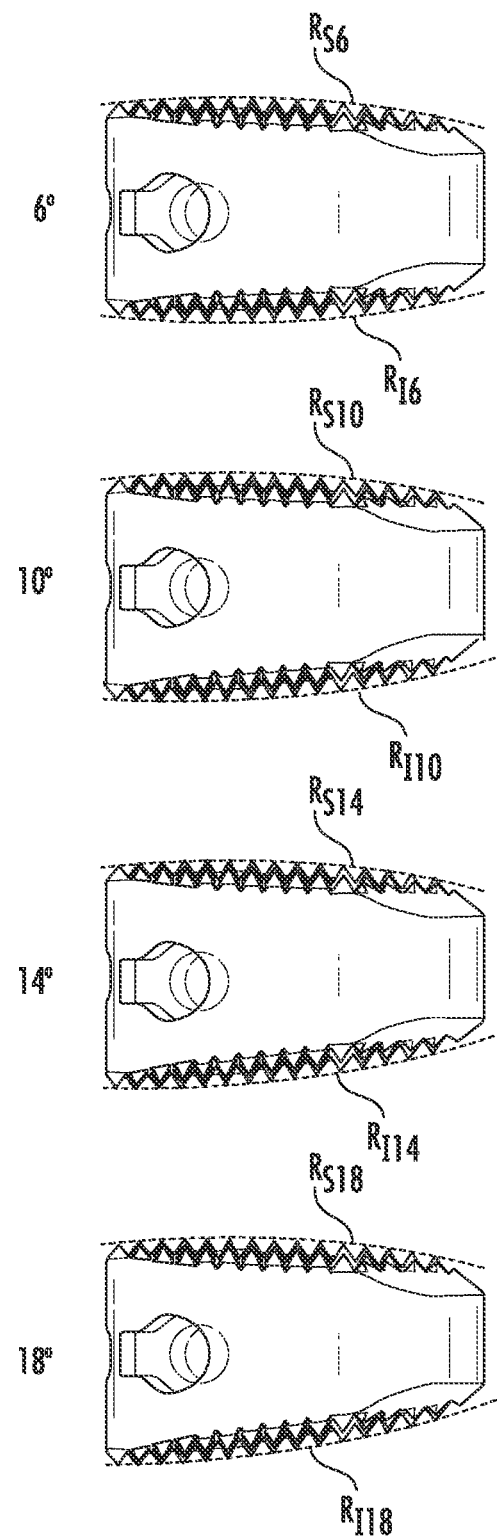
FIG. 1E is a schematic diagram of the left lateral view of the 13.5 mm height small size spacers with different angulation showing the same superior surface convexity and decreasing inferior surface convexity.

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a," "an," and "the," include plural referents unless the context clearly dictates otherwise. The term "comprising" and variations thereof as used herein is used synonymously with the term "including" and variations thereof and are open, non-limiting terms.

The lordosis of the spinal segment increases along the spine. For example in the lumbar region, segment L5/S1 is typically more lordotic than L3/L4. Additionally, as the lordosis increases, the inferior endplate of a given spinal segment typically becomes less convex and more flat the lower the level. For example, for segment L5/S1 the sacral endplate is often flat whereas the L5 endplate can still have some convexity. The spinal implant vertebral spacer described herein provides spacers that have inferior and superior surface angle and convexity variations that are adapted to address the differences in lordosis and endplate surface convexity of the spine. For example, as the lordotic angle of the spacer increases from 6, 10, 14, to 18 degrees, the inferior surface of the spacer becomes less convex in the saggital plane. For the 6 degree spacer the convexity of the superior and inferior surfaces are identical. For the other spacers that have lordotic angles such as 10, 14, and 18 degrees, the inferior surface is less convex than the superior surface. The difference between the convexity of the superior and inferior surface of the spacer increases as the lordotic angle of the spacer increases. The posterior of the spacer comprises chamfers to provide distraction for smoother spacer insertion. The spacer has rounded corners and edges to better match the geometry of the vertebral bodies. The spacers described herein thus provide overall improved fit into vertebral disc space and in some embodiments are even used in the absence of fusion for a prolonged period. The interior of the spacer has channels and undercuts to increase graft volume and retention, support bony ingrowths, and bony stability for better secondary and tertiary stabilization.

Referring to FIG. 1, a left front perspective view of an embodiment of a vertebral spacer 100 is illustrated in FIG. 1A, a right back side perspective view is illustrated in FIG. 1B, a top view is illustrated in FIG. 1C, and a right side view is illustrated in FIG. 1D. Components of the spacer 100 are labeled in FIGS. 1A-D based on the clarity of illustration. Specifically, the spinal implant or spacer 100 comprises a superior surface 102, an inferior surface 104, and a side wall 106 that connects the superior surface 102 and the inferior surface 104 at rounded superior and inferior edges 108 and 110 respectively. The side wall 106 comprises an anterior wall 112 and a posterior wall 114 that are connected by a right lateral wall 116 and a left lateral wall 118. The superior surface 102 and the inferior surface 104 are designed to provide close contact with the upper and lower endplates of neighboring vertebral bodies respectively while the anterior wall 112, the posterior wall 114, the right lateral wall 116, and the left lateral wall 118 are designed to be aligned with the anterior, posterior, right lateral side, and left lateral side of vertebral bodies respectively. As shown in the top view in FIG. 1C, the spacer 100 has curved corners 138a, 138b, 138c, and 138d to provide better anatomical fit into the spine. The superior and the inferior surfaces 102 and 104 are textured and shown to have surface teeth 136. Although the surface teeth are shown to be substantially similar on both surfaces, the texture of the surface is optionally different from each other. In some embodiments, the surface is simply roughened or undulated without obvious protrusions such as the surface teeth 136.

Parameters used to define the specifications of the spacers are shown in FIGS. 1C and 1D. A width of the implant (W) is defined as the longitudinal distance between the centers of the right and left lateral walls as shown in FIG. 1C. A length of the implant (L) is defined as the horizontal distance between the centers of the anterior and posterior walls as shown in FIG. 1C. A height of the implant (H) is defined as a vertical distance between the superior and inferior surfaces at the anterior most edge of the implant 100 accounting for a convexity of the implant 100 and while only taking half of the height of the surface teeth from either surface of the implant into consideration, as shown in FIG. 1D. The posterior wall 114 is shorter than the anterior wall 112 and an angulation α of the spacer is defined as the angle between the superior and the inferior surfaces shown in FIG. 1D. The angulation α of the spacer can be from about 2 to about 30 degrees. The superior and inferior surfaces 102 and 104 of the spacer additionally are convex as shown in FIG. 1D with the convexity of the superior surface defined as the radius of the superior surface curvature (superior radius or $R_S$) and the inferior surface defined as the radius of the inferior surface curvature (inferior radius or $R_I$). Smaller radius corresponds to larger convexity. For example, the spacer 100 shown in FIG. 1D has a superior radius of 95 millimeters and an inferior radius of 150 millimeters, indicating the superior surface is more convex than the inferior surface and the inferior surface is correspondingly flatter than the superior surface.

Spacers with different sizes are designed to fit vertebral bodies of various sizes. The respective radius of curvature values of the superior and inferior surfaces diverge as angulation between the superior and the inferior surfaces increases. For example, small, medium, and large size spacers are listed in Table 1 below showing the specification of the width, length, height, angulation, superior radius, and inferior radius of the spacers. As will be recognized, the width to length ratio of each of the spacer types is approximately 1.28 and may range from 1.25 to 1.35.

TABLE 1

| SPACER TYPE | WIDTH (mm) | LENGTH (mm) | SUPERIOR RADIUS (mm) | ANGLE (°) | HEIGHT (mm) | INFERIOR RADIUS(mm) |
|---|---|---|---|---|---|---|
| Small | 32 | 25 | 85 | 6 | 9, 10.5, 12, 13.5, 15, 17, 19 | 85 |
|  |  |  |  | 10 | 10.5, 12, 13.5, 15, 17, 19 | 110 |
|  |  |  |  | 14 | 12, 13.5, 15, 17, 19 | 150 |
|  |  |  |  | 18 | 13.5, 15, 17, 19 | 200 |
| Medium | 36 | 28 | 90 | 6 | 9, 10.5, 12, 13.5, 15, 17, 19 | 90 |
|  |  |  |  | 10 | 10.5, 12, 13.5, 15, 17, 19 | 130 |
|  |  |  |  | 14 | 12, 13.5, 15, 17, 19 | 175 |
|  |  |  |  | 18 | 13.5, 15, 17, 19 | 225 |
| Large | 40 | 31 | 95 | 6 | 9, 10.5, 12, 13.5, 15, 17, 19 | 95 |
|  |  |  |  | 10 | 10.5, 12, 13.5, 15, 17, 19 | 150 |
|  |  |  |  | 14 | 12, 13.5, 15, 17, 19 | 200 |
|  |  |  |  | 18 | 13.5, 15, 17, 19 | 250 |

Although example value for each specific parameters of the spacers are outlined in Table 1, any reasonable value for a given parameter is contemplated and is within the scope of the present disclosure. For example, for spacers that have angulation between about 2 degrees to about 6 degrees, the superior radius and the inferior radius of the spacer are designed to be similar to each other. For spacers that have angulation between about 6 degrees and about 30 degrees, the inferior radius of the spacer is designed to be at least 20% larger than the superior radius, in some embodiments at least 30% larger, in some embodiments at least 40% larger, in further embodiments at least 50% larger, in additional embodiments at least 60% larger. The variation in inferior radius based on angulation is consistent with the lordosis of the vertebral bodies along the spine, making the spacer have better fit with the neighboring vertebral bodies.

Specifically, the small spacer has width of 32 mm and length of 25 mm. The medium spacer has width of 36 mm and length of 28 mm. The large spacer has width of 40 mm and length of 31 mm. The small spacer has smaller radius than the corresponding medium and large spacer. The superior radius ($R_S$) for a given spacer size is the same with 85 millimeters for all small size spacers, 90 millimeters for all medium size spacers, and 95 millimeters for all large size spacers. Each spacer size is designed to have for example four angulations, i.e. 6, 10, 14 and 18 degrees where possible. Depending on the angulation, different height options are designed with more height options available for smaller angles. In some embodiments, as the spacer angulation increases, the inferior radius ($R_I$) of the spacer increases also. Although within each angulation, the inferior radius may remain the same regardless of the height difference. For example, for the small size spacers, the inferior radius increases from 85 millimeters at 6 degree angulation to 110, 150, and 200 millimeters at 10, 14, and 18 degree angulations respectively regardless of the difference in height. For the medium size spacers, the inferior radius increases from 90 millimeters at 6 degree angulation to 130, 175, and 225 millimeters at 10, 14, and 18 degree angulations respectively regardless of the difference in height. For the large size spacers, the inferior radius increases from 95 millimeters at 6 degree angulation to 150, 200, and 250 millimeters at 10, 14, and 18 degree angulations respectively regardless of the difference in height.

Referring to FIG. 1E, left lateral side views of example spacers with 6, 10, 14, and 18 angulations are illustrated. The convexities of the superior and inferior surfaces of the spacer are indicated with dashed lines. While the convexity of the superior surfaces RS6, RS10, RS14, and RS18 are the same, the convexity of inferior surfaces RI6, RI10, RI14, and RI18 decreases as the angulation increases and become more flat.

The anterior wall 112 of the spacer 100 comprises a diamond shaped hexagon depression 120 adapted to receive an insertion tool 122 shown in FIG. 1F. In FIGS. 1A and 1C, the spacer 100 is shown to have two vertical through-channels 124 and 126 extending through the implant or spacer from the superior surface 102 to the inferior surface 104 with a vertical strut 128 vertically separating the channels 124 and 126 while maintaining contacted with the side wall 106. The strut 128 further comprises a window 148 that provides connection between the two through-channels. The superior surface 102 of the spacer 100 is shown to have grooves 130 and 132 that are substantially parallel to the sides 116 and 118 of the spacer 100. Similar grooves present on the inferior surface 104 and is discussed with relevant figure illustration below. The grooves on the surfaces of the spacer 100 provide guidance for rails of insertion tools.

Figure 1G:
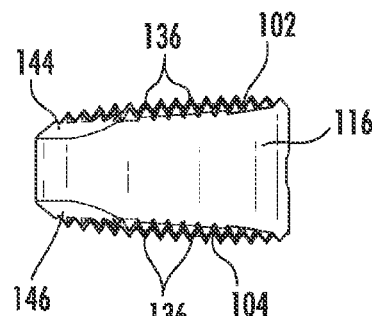
FIG. 1G is a schematic diagram of a left side view showing the right lateral wall of the spacer of FIG. 1A.
Figure 1H:
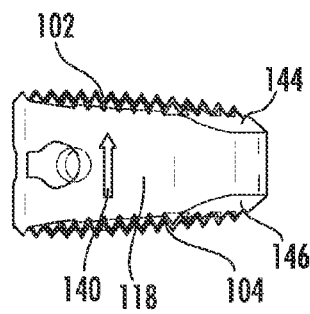
FIG. 1H is a schematic diagram of a right side view showing the left lateral wall of the spacer of FIG. 1A.
Figure 1I:
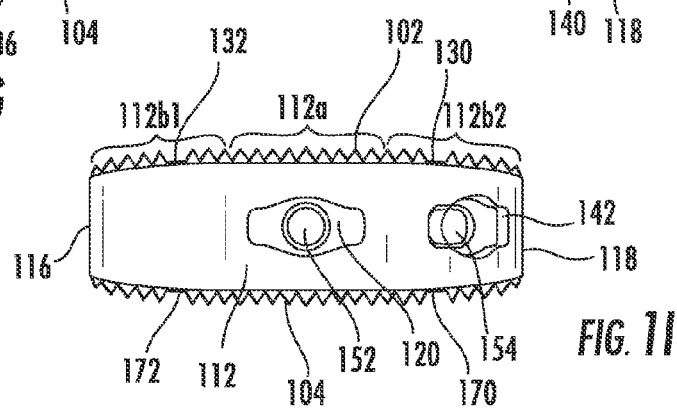
FIG. 1I is a schematic diagram of a front view showing the anterior wall of the spacer of FIG. 1A.

The left side, the right side, the front, and the back views of the spacer 100 showing the right lateral wall, the left lateral wall, the anterior wall, and the posterior wall are illustrated in FIGS. 1G, 1H, 1I, and 1J respectively. Referring to FIG. 1G, the view of the right lateral wall 116 is illustrated showing the surface teeth 136. Referring to FIG. 1H, the view of the left lateral wall 118 is illustrated showing an arrow marking 140, indicating the upside of the arrow being the superior surface of the implant. The view of the anterior wall 112 is illustrated in FIG. 1I showing the diamond shaped hexagon depression 120 at the front center. An additional side depression 142 at the 45 degree off the horizontal mid line of the spacer is also shown. While the front center depression is used for delivering the spacer via the anterior of the spine, the 45 degree depression 142 is used for delivering the spacer via the anterior-left lateral side of the spine. The anterior wall 112 comprises a middle portion 112a, a first side portion 112b1 that merges into the right lateral wall 116 and a second side portion 112b2 that merges into the left lateral wall 118. The first and the second portions 112b1 and 112b2 are shown to curve with equal radius while the middle portion 112a is straight or less curved compared to the two side portions. The curved first and second portions of the anterior wall provide a more anatomically friendly footprint for the spacer to provide a better fit in the spine.

Figure 1J:
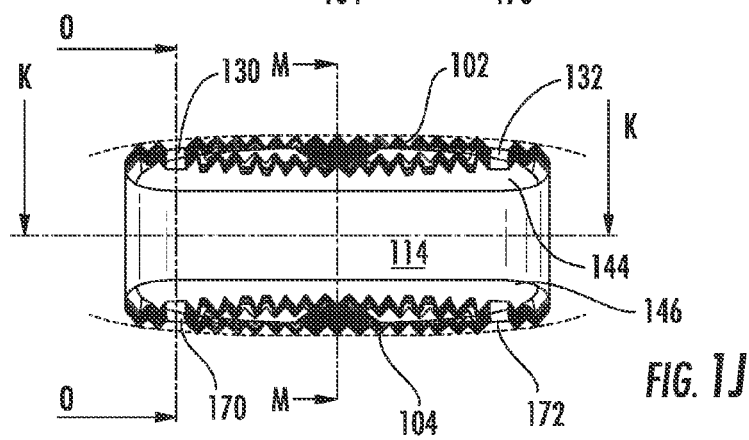
FIG. 1J is a schematic diagram of a back view showing the posterior wall of the spacer of FIG. 1A.

The view of the posterior wall 114 of the spacer is illustrated in FIG. 1J, showing the anterior wall 112 taller than the posterior wall 114. The side portions of the posterior wall are similarly curved as the anterior wall to additionally provide a more anatomically friendly footprint for the spacer to provide a better fit in the spine. To provide better insertion dynamic, the posterior wall 114 is chamfered with posterior superior chamfer 144 and posterior inferior chamfer 146. The chamfers 144 and 146 are shown in FIGS. 1G and 1H as providing a "bullet nose" shape to the posterior of the spacer. The embodiment illustrated in FIGS. 1G and 1H shows both posterior superior chamfer and posterior inferior chamfer having a 45 degree angle as an example. In some embodiments, the superior chamfer and the inferior chamfer have angles from 30 degrees to 45 degrees. The superior chamfer and the inferior chamfer on the posterior wall can have the same or different pathways or angles. For example, in some embodiments, the superior chamfer has a 45 degree angle while the inferior chamfer has a 30 degree angle. Both the anterior and posterior views also reveal the grooves 130 and 132 on the superior surface 102 and grooves 170 and 172 on the inferior surface 104 for the placement of insertion tool. The grooves 130 and 132 on the superior surface 102 are shown to align with grooves 170 and 172 on the inferior surface 104 respectively, which is one example of the position and shape of the grooves. In other embodiments, the grooves on the superior surface are not aligned with the grooves on the inferior surface.

Figure 1K:
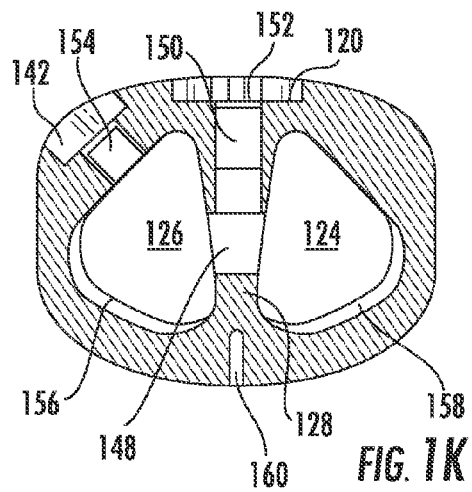
FIG. 1K is a schematic diagram of a horizontal cross sectional view of the vertebral spacer of FIG. 1A along the line K-K of FIG. 1J.
Figure 1L:
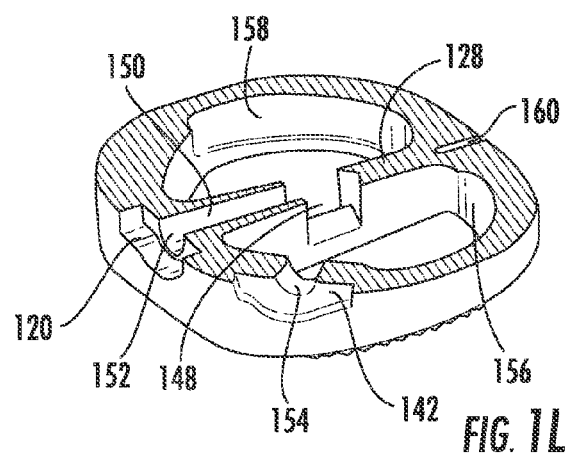
FIG. 1L is a schematic diagram of a perspective view of FIG. 1K.

The view of the spacer along the K-K line of FIG. 1J is illustrated in FIG. 1K, showing the top view of the horizontal cross section of the spacer. A perspective view of the horizontal cross section of the spacer is shown in FIG. 1L, providing further illustration of the inner components of the spacer. Specifically, the horizontal cross section is shown to have the front center depression 120 and the side depression 142 offset at 45 degree to each other. The window 148 in the strut 128 is shown to connect the two channels 124 and 126, which allows bony fusion between the two bony pillars formed in the two through channels 124 and 126 during the secondary and tertiary phases of the bony fusion. The depressions 120 and 142 have threaded openings 152 and 154 for threaded engagements with an insertion tool. The cross sectional view further reveals a channel 150 providing connection between the window 148 and the opening 152 of the front center depression 120. The channel 150 provides communication between the substances inside the through-channels and the exterior of the spacer. The opening 154 of depression 142 is shown to be connected with the through channel 124, providing additional communication between the substances inside the through channels and the exterior of the spacer. The through-channels 124 and 126 further comprise undercuts 156 and 158 to increase graft volume and retention, and to support bony ingrowths and bony stability. The channel 150, the undercuts 156, 158 as well as openings 152 and 154 collectively provide overall better stabilization during secondary and tertiary phases of the bony fusion.

Figure 1M:
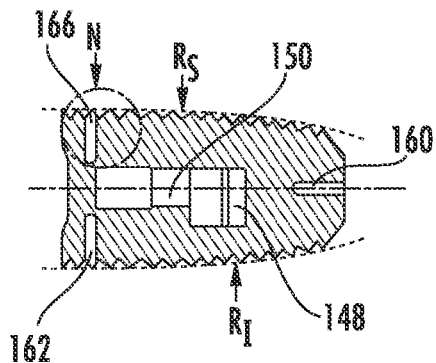
FIG. 1M is a schematic diagram of a cross sectional view of the vertebral spacer of FIG. 1A along the line M-M of FIG. 1J.
Figure 1N:
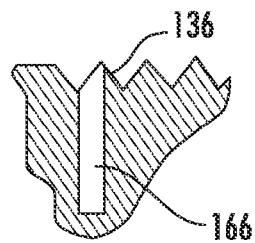
FIG. 1N is an enlarged view of the circled portion N of FIG. 1M.

Radio-opaque markers can be embedded inside the spacer to help visualize the placement of the spacer in the spine. FIG. 1B for example reveals one posterior horizontal radio-opaque marker 160 positioned through the center of the posterior wall, two vertical radio-opaque markers 162 and 164 positioned in the anterior wall inferior and two vertical markers 166 and 168 positioned in the anterior wall superior. Referring to FIG. 1M, a mid-line cross sectional view of the spacer along the M-M line of FIG. 1C is illustrated. Cross sectional side view of the anterior superior radio-opaque marker 166, anterior inferior radio-opaque marker 162, and posterior horizontal radio-opaque marker 160 are shown in FIG. 1M. FIG. 1M also provides side views of the channel 150 connected with the window 148. A portion of FIG. 1M indicated by circle N is enlarged in FIG. 1N, showing the radio-opaque marker 166 fully embedded inside the spacer body under surface teeth 136.

Figure 1O:
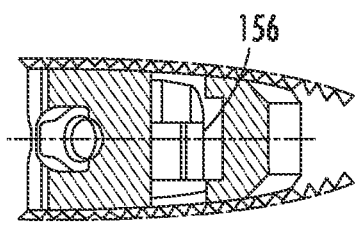
FIG. 1O is a cross sectional view along O-O line of FIG. 1J revealing undercut.
Figure 1P:
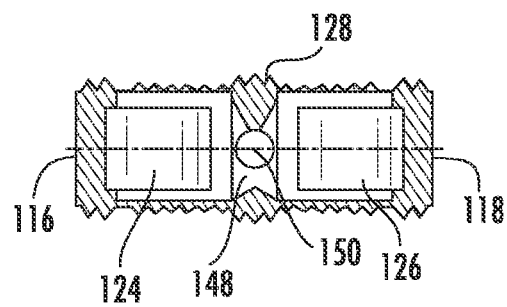
FIG. 1P is a cross sectional view along P-P line of FIG. 1D.
Figure 1Q:
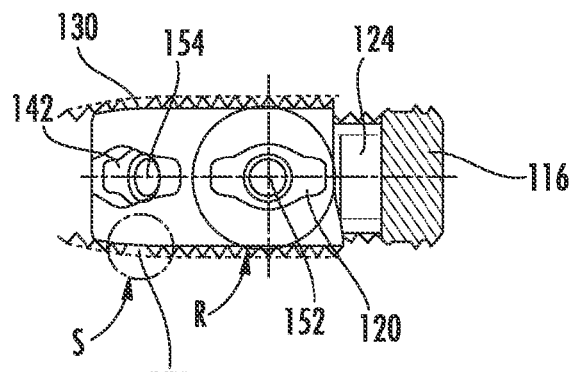
FIG. 1Q is a partial cross sectional view along the Q-Q line of FIG. 1C.
Figure 1R:
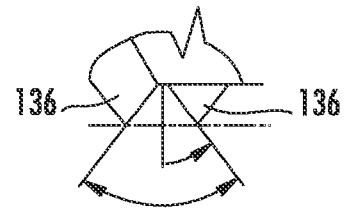
FIG. 1R is an enlarged view of two neighboring surface teeth 136.
Figure 1S:
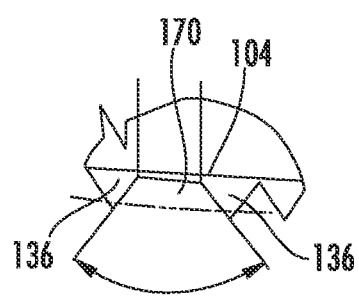
FIG. 1S is an enlarged view of the circled portion S of FIG. 1Q.

The cross sectional view along O-O line of FIG. 1J is illustrated in FIG. 1O, showing the undercut 156. The cross sectional view along the P-P line of FIG. 1D is illustrated in FIG. 1P, showing the through-channels 124 and 126, cross sectional view of the left lateral wall 118, cross sectional view of the right lateral wall 116, cross sectional view of the channel 150, window 148, and the strut 128. A partial cross sectional view along the Q-Q line of FIG. 1C is illustrated in FIG. 1Q, showing the through-channel 124, revealing a cross section of the right lateral wall 116, the front center depression 120 with threaded opening 152 and lateral depression 142 with threaded opening 154. The portion of the right lateral wall 116 revealed in FIG. 1Q appears to be thicker than the portion revealed in FIG. 1P, consistent with the illustration in FIG. 1C that the thickness of the lateral walls varies, with the anterior portion of the wall thicker than the middle and posterior portion. Circled portions R and S of FIG. 1Q are enlarged in FIGS. 1R and 1S respectively, showing the triangular cross section of the surface teeth 136. The height of the teeth is shown to be 0.86 mm in FIG. 1R and the angle between the teeth is 37 degrees. The portion of the superior surface illustrated in FIG. 1S shows the groove 170 on the inferior surface 104 without the surface teeth 136.

Figure 2A:
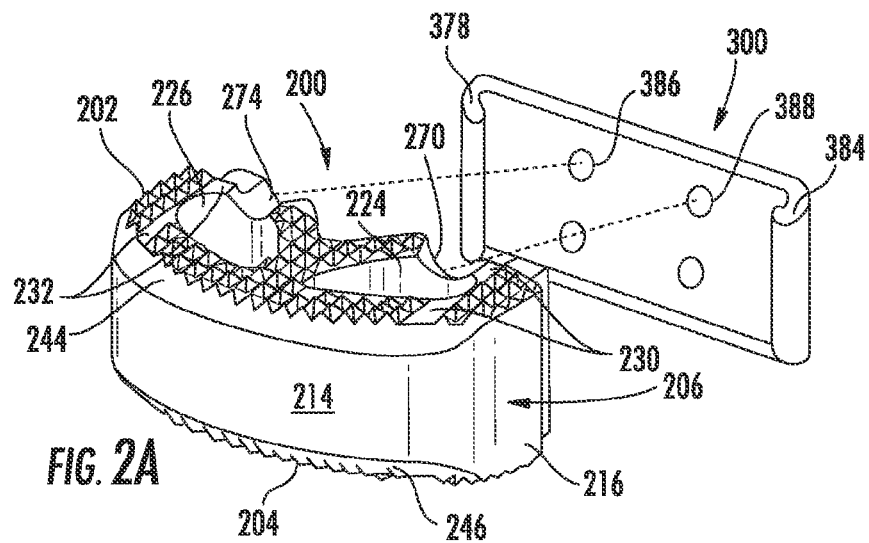
FIG. 2A is a schematic diagram of a left front perspective view of a vertebral spacer to be used in conjunction with an anchor plate.
Figure 2B:
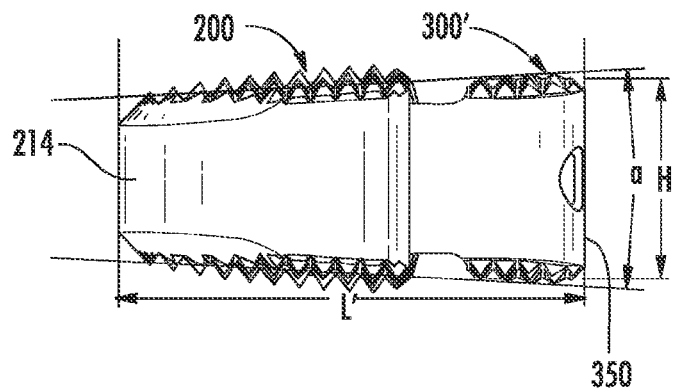
FIG. 2B is a schematic diagram of a left side view of the spacer of FIG. 2A integrated with an anchor plate.
Figure 2C:
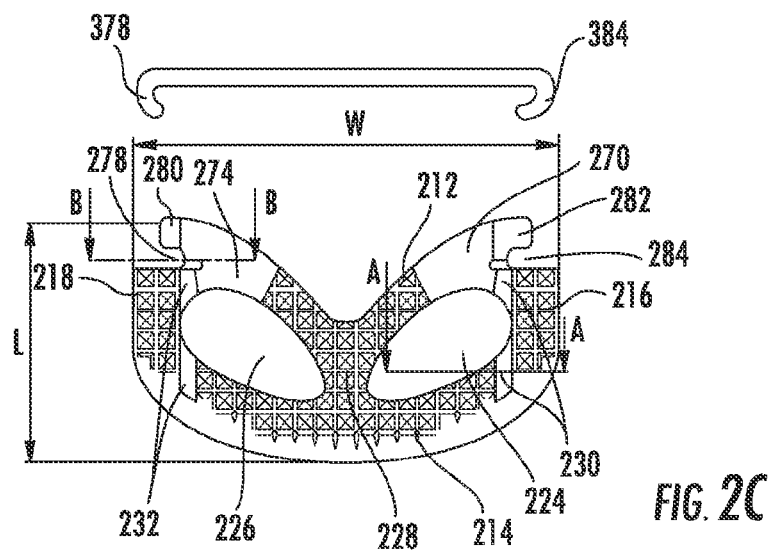
FIG. 2C is a schematic diagram of a top view of the spacer of FIG. 2A.
Figure 2D:
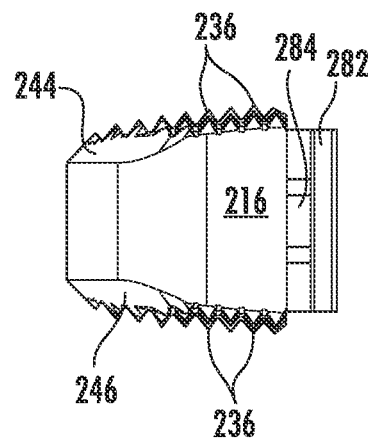
FIG. 2D is a schematic diagram of a left side view showing the right lateral wall of the spacer of FIG. 2A.
Figure 2E:
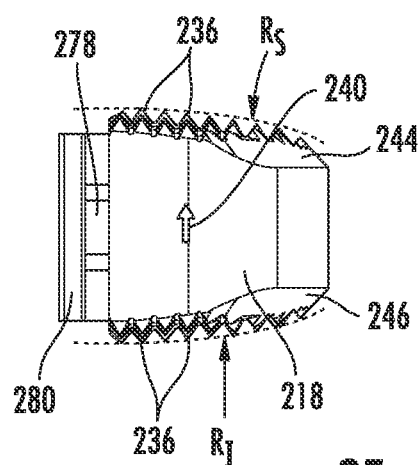
FIG. 2E is a schematic diagram of a right side view showing the left lateral wall of the spacer of FIG. 2A.

The spinal implant or spacer disclosed herein is optionally designed to be interfaced with an anchor plate. Referring to FIGS. 2A-E, a left front perspective view of an embodiment of a vertebral spacer 200 with an anchor plate 300 is illustrated in FIG. 2A, a vertebral spacer 200 with an anchor plate 300' is illustrated in FIG. 2B, a top view is illustrated in FIG. 2C, a left side view of the spacer 200 is illustrated in FIG. 2D, and a right side view of the spacer 200 is illustrated in FIG. 2E. Components of the spacer 200 are labeled in FIGS. 2A-E based on the clarity of illustration. Specifically, the spinal implant or spacer 200 comprises a superior surface 202, an inferior surface 204, and a side wall 306 that connects the superior surface 202 and the inferior surface 204. The side wall 206 comprises a posterior wall 214 connected to a right lateral wall 216 and a left wall 218. The lateral walls are in turn connected to the top open ends of a "V" shaped anterior wall 212 with the bottom tip of the "V" connected to the posterior wall in the form of a vertical strut 228 separating the two through-channels 224 and 226. The superior surface 202 of the spacer 200 is shown to have grooves 230 and 232 that are substantially parallel to the sides 216 and 218 of the spacer 100. Similar grooves present on the inferior surface 204 and is discussed with relevant figure illustration below. The grooves on the surfaces of the spacer 200 provide guidance for rails of insertion tools.

The superior surface 202 and the inferior surface 204 are designed to provide close contact with the upper and lower endplates of neighboring vertebral bodies respectively while the anterior wall 212 interfaced with the anchor plate, the posterior wall 214, the right lateral wall 216, and the left lateral wall 218 are designed to be aligned with the anterior, posterior, right lateral side, and left lateral side of vertebral bodies respectively. The superior and the inferior surfaces are textured and shown to have surface teeth 236. Although the surface teeth are shown to be substantially similar on both surfaces, the texture of the surface is optionally different from each other. In some embodiments, the surface is simply roughened or undulated without obvious protrusions such as the surface teeth 236.

Referring to FIG. 2D, the view of the right lateral wall 216 is illustrated showing the surface teeth 236. Referring to FIG. 2E, the view of the left lateral wall 218 is illustrated showing an arrow marking 240 to indicate the upside of the arrow being the superior surface of the implant. The spacer 200 also comprises two vertical recesses 278 and 284 along the lateral walls 218 and 216 respectively proximate the connections between the posterior wall and the lateral walls. The ends of the sides of the "V" shape of the anterior wall 212 are shown as protrusion 280 adjacent to recess 278 and protrusion 282 adjacent to recess 284. Collectively, the protrusion-recess pairs 280-278 and 282-284 enables the spacer to mate with inward pointing projections 378 and 384 of an anchor plate 300 respectively. Side views of the protrusion-recess pairs 280-278 and 282-284 are shown in FIGS. 2D and 2E respectively. Holes 386 and 388 on the anchor plate 300 are shown to be aligned with the superior indentations 274 and 270 of the spacer 200 respectively in FIG. 2A.

Figure 2F:
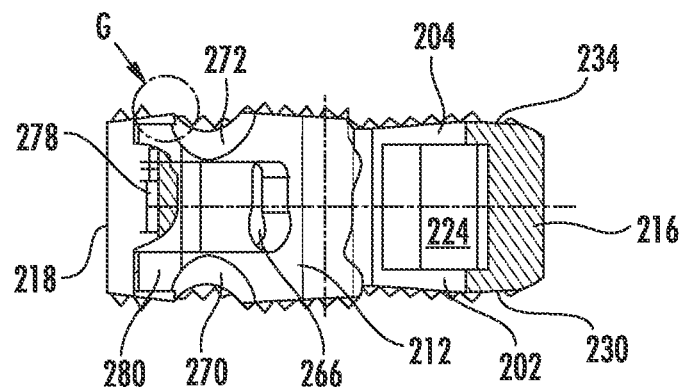
FIG. 2F is a partial cross sectional view along the A-A and B-B lines of FIG. 2C.
Figure 2G:
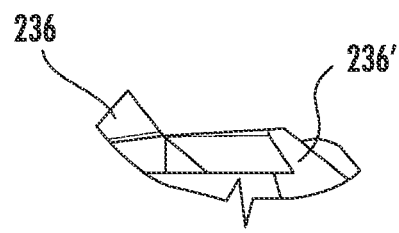
FIG. 2G is an enlarged view of the circled portion G of FIG. 2F.

The view of the spacer 200 along the A-A and B-B lines of FIG. 2C is illustrated in FIG. 2F, showing the through-channel 224, revealing a cross section of the right lateral wall 216 along A-A line, the front view of the remaining posterior wall 212 revealing a window 266 that provides communication between the through channel 226 and the exterior of the spacer 200. The view along the B-B line reveals a partial cross section of the posterior wall 212 revealing the protrusion 280, the recess 278, and the left lateral wall 218. FIG. 2F additionally reveals superior surface groove 230, the inferior surface groove 234 on the right lateral side and superior indentation 270 and inferior indentation 272 on the left lateral side. Corresponding right lateral side superior groove 232 and superior indentation 274 are shown in FIGS. 2A and 2C. The superior surface indentions 270 and 274 provide space for a fixation mechanism such as screw, nails, etc. to anchor the anchor plate 300 with upper vertebral endplates when the vertical recesses 278 and 284 mate with respective inward pointing projections 378 and 384 respectively. The corresponding inferior surface indentions 272 and 276 provide space for fixation mechanism to anchor the anchor plate 300 with lower vertebral endplates when the vertical recesses 278 and 284 mate with respective inward pointing projections 378 and 384 respectively. An enlarged view of the portion of FIG. 2F circled in G is shown in FIG. 2G, showing the variation of surface teeth 236 and 236'.

Parameters used to define the specifications of the spacers are shown in FIGS. 2B and 2C. A width of the spacer (W) is defined as the longitudinal distance between the centers of the right and left lateral walls as shown in FIG. 2C. A length of the spacer (L) is defined as the horizontal distance between the centers of the anterior and posterior walls as shown in FIG. 2C. The length of the entire or overall implant including the spacer and the anchor plate (L') is defined as the horizontal distance between the centers of the posterior wall 214 and an anterior wall 350 of the anchor plate 300' as show in FIG. 2B. The height of the implant (H) is defined as a vertical distance between the superior and inferior surfaces at the anterior most edge of the implant 200 accounting for the convexity of the implant 200 and while only taking half of the height of the surface teeth from either surface of the implant into consideration as shown in FIG. 2B. The posterior wall 214 is shorter than the anterior wall 212 and an angulation α of the spacer is defined as the angle between the superior and the inferior surfaces shown in FIG. 2B. The angulation α of the spacer can be from about 2 to about 30 degrees as shown in FIG. 2B. The superior and inferior surfaces 202 and 204 of the spacer additionally are convex as shown in FIG. 2E with the convexity of the superior surface defined as the radius of the superior surface curvature (superior radius or $R_S$) and the inferior surface defined as the radius of the inferior surface curvature (inferior radius or $R_I$). Smaller radius corresponds to larger convexity.

Spacers with different sizes are designed to fit vertebral bodies of various sizes. For example, small, medium, and large size spacers are listed in Table 2 below showing the specification of the width, height, angulation, superior radius, and inferior radius of the spacers. The length listed in Table 2 is the overall implant length L' discussed above. As will be recognized, the width (W) to overall all length (L') ratio of each of the spacer types is approximately 1.28 and may range from 1.25 to 1.35.

TABLE 2

| SPACER TYPE | WIDTH (mm) | L' (mm)* | SUPERIOR RADIUS (°) | ANGLE (°) | HEIGHT (mm) | INFERIOR RADIUS(°) |
|---|---|---|---|---|---|---|
| Small | 32 | 25-28 | 85 | 6 | 10.5, 12, 13.5, 15, 17, 19 | 85 |
|  |  |  |  | 10 | 10.5, 12, 13.5, 15, 17, 19 | 110 |
|  |  |  |  | 14 | 12, 13.5, 15, 17, 19 | 150 |
| Medium | 36 | 28-31 | 90 | 6 | 10.5, 12, 13.5, 15, 17, 19 | 90 |
|  |  |  |  | 10 | 10.5, 12, 13.5, 15, 17, 19 | 130 |
|  |  |  |  | 14 | 12, 13.5, 15, 17, 19 | 175 |
| Large | 40 | 31-34 | 95 | 6 | 10.5, 12, 13.5, 15, 17, 19 | 95 |
|  |  |  |  | 10 | 12, 13.5, 15, 17, 19 | 150 |
|  |  |  |  | 14 | 12, 13.5, 15, 17, 19 | 200 |

*The thickness of the anchor plate 300 may vary depending on a depth of the inward pointing projections 378 and 384. As such, the overall length L' of the assembled spacer or implant may vary within a range, as indicated.

Although example value for each specific parameters of the spacers with anchor plates are outlined in Table 2, any reasonable value for a given parameter is contemplated and is within the scope of the present disclosure. For example, for spacers that have angulation between about 2 degrees to about 6 degrees, the superior radius and the inferior radius of the spacer are designed to be similar to each other. For example, spacers that have angulation between about 6 degrees and about 30 degrees, the inferior radius of the spacer may be designed to be at least 20% larger than the superior radius, in some embodiments at least 30% larger, in some embodiments at least 40% larger, in further embodiments at least 50% larger, in additional embodiments at least 60% larger. The variation in inferior radius based on angulation is consistent with the lordosis of the vertebral bodies along the spine, making the spacer have better fit with the neighboring vertebral bodies.

The back view of the spacer 200 showing the posterior wall 214 is illustrated in FIG. 2H, showing the anterior wall 212 taller than the posterior wall 214. The side portions of the posterior wall are curved to provide a more anatomically friendly footprint for the spacer to provide a better fit in the spine. To provide better insertion dynamic, the posterior wall 214 is chamfered with posterior superior chamfer 244 and posterior inferior chamfer 246. The chamfers 244 and 246 are shown in FIGS. 2C and 2D as providing a "bullet nose" shape to the posterior of the spacer. The embodiment illustrated in FIGS. 2C and 2D shows both posterior superior chamfer and posterior inferior chamfer having a 45 degree angle as an example. In some embodiments, the superior chamfer and the inferior chamfer have angles from 30 degrees to 45 degrees. The superior chamfer and the inferior chamfer on the posterior wall can have the same or different pathways or angles. For example, in some embodiments, the superior chamfer has a 45 degree angle while the inferior chamfer has a 30 degree angle. The anterior and posterior views also reveal the grooves 230 and 232 on the superior surface 202 and grooves 234 and 238 on the inferior surface 204 for the placement of insertion tool. The grooves 230 and 232 on the superior surface 202 are shown to align with grooves 234 and 238 on the inferior surface 204 respectively, which is one example of the position and shape of the grooves. In other embodiments, the grooves on the superior surface are not necessarily aligned with the grooves on the inferior surface.

The view of the spacer 200 along the I-I line of FIG. 2H is illustrated in FIG. 2I, showing the top view of the horizontal cross section of the spacer 200. Unlike spacer 100, the two through channels 224 and 226 of spacer 200 are shown to remain separated by strut 228, which does not have a window to allow bony fusion between the two bony pillars formed in the two through channels 224 and 226 during the secondary and tertiary phases of the bony fusion. Instead, the two sides of the "V" shape of the anterior wall 212 is shown to have window 264 in communication with through-channel 224 and window 266 in communication with through-channel 226. The windows 264 and 266 provide communication between the substances inside the through-channels and the exterior of the spacer 200. The cross section also reveals radio-opaque marker 260 embedded horizontally inside the posterior section of the spacer 200.

The view of the spacer 200 along the J-J line of FIG. 2H is illustrated in FIG. 2JI, showing the side view of the vertical cross section of the spacer 200. The vertical cross section of the strut 228 is shown to be solid without window or additional channel. Radio-opaque marker 260 is shown to be partially embedded inside the strut 228 also. The circled portion K of the superior surface 202 in FIG. 2K is enlarged, showing enlarged view of the surface teeth 236. Perspective views of the spacer 200 along the arrows L and M in reference to dot 298 are shown in FIGS. 2L and 2M respectively. The view in FIG. 2L reveals the window 266 on the posterior wall 214, right lateral inferior indentation 276 on inferior surface 204. The view in FIG. 2M reveals the window 264 on the posterior wall 214, left lateral inferior indentation 272 on inferior surface 204.

In the above spacers 100 and 200, any bio-compatible material may be used. For example, the spacers 100 and 200 may be composed of polyether ether ketone (PEEK), titanium alloy, medical grade plastic, PEKEKK (polyetherketoneetherketoneketone), ceramic, and/or poly-L-lactide acid (PLLA). In some implementations, the spacers 100 and 200 may have coatings such as hydroxyapatite.

Many modifications and other embodiments of the disclosure set forth herein will come to mind to one skilled in the art to which this disclosure pertains having the benefit of the teachings presented in the foregoing description. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A spinal implant for insertion between adjacent upper and lower vertebral endplates, the spinal implant comprising:
   superior and inferior surfaces for contacting the upper and lower endplates respectively with each surface comprising a plurality of surface teeth;
   a side wall connecting the superior and inferior surfaces, wherein the side wall comprises an anterior wall and a posterior wall that are connected by a right lateral wall and a left lateral wall, wherein the posterior wall is shorter than the anterior wall such that an angulation between the superior and the inferior surfaces is from about 2 to about 30 degrees;
   at least one recessed surface formed in the anterior wall, the recessed surface being adapted to receive an insertion tool; and
   vertical through-channels extending through the implant from the superior surface to the inferior surface with at least one vertical strut separating the channels,
   wherein a width of the implant is defined as a longitudinal distance between the centers of the right and left lateral walls, a length of the implant is defined as a horizontal distance between the centers of the anterior and posterior walls, and a height of the implant is defined as a vertical distance between the superior and inferior surfaces at an anterior most edge of the implant, the height accounting for a convexity of the superior and inferior surfaces and including one-half of a height of the surface teeth disposed on the superior and inferior surfaces, and
   wherein the superior and inferior surfaces are convex having respective radius of curvature values defined in a sagittal plane of the implant, the superior radius of curvature value varies from the inferior radius of curvature value, such that the superior and inferior surfaces have different angulation.

2. The implant of claim 1, wherein if the angulation is less 6 degrees, then the superior radius and inferior radius are substantially similar to each other.

3. The implant of claim 1, wherein if the angulation is greater than 6 degrees, then the inferior radius is at least 20% larger than the superior radius.

4. The implant of claim 1, wherein the width to length ratio of the implant is between 1.35 and 1.25 and the height of the implant is between about 9 mm and 19 mm.

5. The implant of claim 4, wherein the width is between about 32 mm and 40 mm and wherein the length is between about 25 mm and 34 mm.

6. The implant of claim 4, wherein the angulation between the superior and inferior surfaces is greater than about 6 degrees, the inferior radius is greater than the superior radius.

7. The implant of claim 6, wherein the superior and inferior radiuses are between about 85 mm and about 95 mm.

8. The implant of claim 4, wherein the angulation between the superior and inferior surfaces is about 10 degrees, a ratio of the superior radius to the inferior radius is between about 0.63 and 0.77.

9. The implant of claim 8, wherein the superior radius is between about 85 mm to 95 mm and the inferior radius is between about 110 mm and 150 mm.

10. The implant of claim 4, wherein the angulation between the superior and inferior surfaces is about 14 degrees, a ratio of the superior radius to the inferior radius is between about 0.47 and 0.56.

11. The implant of claim 10, wherein the superior radius is between about 85 mm to 95 mm and the inferior radius is between about 150 mm and 200 mm.

12. The implant of claim 4 wherein the angulation between the superior and inferior surfaces is about 18 degrees, a ratio of the superior radius to the inferior radius is between about 0.38 and 0.42.

13. The implant of claim 12, wherein the superior radius is between about 85 mm to 95 mm and the inferior radius is between about 200 mm and 250 mm.

14. The implant of claim 1, wherein the vertical strut comprises a window that provides connection between the two through-channels,
   wherein the implant further includes:
      at least one opening formed on the recessed surface of the anterior wall, the opening being adapted to receive an insertion tool;
      a channel formed adjacent the recessed surface providing connection between the opening and the window; and
      a threaded portion located between the at least one opening and the channel.

15. The implant of claim 1, wherein the through-channels further include undercuts protruding within the through-channels and proximate to the inferior surface.

16. The implant of claim 1, wherein the anterior wall comprises a middle portion, a first side portion merges into the right lateral wall and a second side portion merges into the left lateral wall, wherein the first and the second portions are curved with equal radius and the middle portion is substantially straight or less curved as compared to the two side portions.

17. The implant of claim 1, wherein the posterior wall comprises a middle portion, a first side portion merges into the left lateral wall and a second side portion merges into the right lateral wall, wherein the first and the second portions are curved with equal radius and the middle portion is straight or less curved compared to the two side portions.

18. The implant of claim 1, wherein the posterior wall further comprises superior chamfer and inferior chamfer at the interfaces with the superior surface and the inferior surface respectively.

19. The implant of claim 18, wherein the superior chamfer and the inferior chamfer on the posterior wall are formed at angles from 30 degrees to 45 degrees.

20. The implant of claim 1, wherein the recessed surface is a diamond-shaped hexagon and is positioned proximate to a center of the anterior wall, the recessed surface having a longitudinal length that is perpendicular to the lateral walls.

21. The implant of claim 20, further comprising at least one second diamond-shaped hexagon recess on the anterior and left lateral walls at approximately a 45 degree angle from the center of the anterior wall.

22. A spinal implant, comprising:
   a body having a side wall, a superior surface, and an inferior surface, wherein the side wall comprises an anterior wall and a posterior wall that are connected by a right lateral wall and a left lateral wall, wherein the posterior wall is shorter than the anterior wall such that an angulation between the superior and the inferior surfaces is from about 2 to about 30 degrees;
a vertical strut that extends from an interior surface of the right lateral wall to an interior surface of the left lateral wall forming a plurality of vertical through-channels within the body, the vertical through-channels further comprising undercuts that extend inwardly proximate to the inferior surface within the through-channels; and
at least one recessed surface formed in the anterior wall, the recess being adapted to receive an insertion tool,
wherein the superior and inferior surfaces are convex having respective radius of curvature values defined in a sagittal plane of the implant, where the superior radius of curvature value varies from the inferior radius of curvature value, such that the superior and inferior surfaces have different angulation.

23. The implant of claim 22, wherein if angulation between the superior and inferior surfaces is less than 6 degrees, then the superior radius and inferior radius are substantially similar to each other.

24. The implant of claim 22, wherein the angulation between the superior and inferior surfaces is greater than 6 degrees, then the inferior radius is at least 20% larger than the superior radius.

25. The implant of claim 22, wherein a width of the implant is defined as a longitudinal distance between the centers of the right and left lateral walls, a length of the implant is defined as a horizontal distance between the centers of the anterior and posterior walls, and a height of the implant is defined as a vertical distance between the superior and inferior surfaces at an anterior most edge of the implant, the height accounting for a convexity of the superior and inferior surfaces and including one-half of a height of the surface teeth disposed on the superior and inferior surfaces.

26. The implant of claim 25, wherein the width to length ratio of the implant is between 1.35 and 1.25 and the height of the implant is between about 9 mm and 19 mm.

27. The implant of claim 25, wherein the angulation between the superior and inferior surfaces is about 6 degrees, the inferior radius is greater than the superior radius.

28. The implant of claim 25, wherein the angulation between the superior and inferior surfaces is about 10 degrees, a ratio of the superior radius to the inferior radius is between about 0.63 and 0.77.

29. The implant of claim 25, wherein the angulation between the superior and inferior surfaces is about 14 degrees, a ratio of the superior radius to the inferior radius is between about 0.47 and 0.56.

30. The implant of claim 25 wherein the angulation between the superior and inferior surfaces is about 18 degrees, a ratio of the superior radius to the inferior radius is between about 0.38 and 0.42.

31. The implant of claim 22, wherein the vertical strut comprises a window that provides connection between the two through-channels,
wherein the implant further includes:
a least one opening formed on the recessed surface of the anterior wall, the opening being adapted to receive an insertion tool; and
a channel formed adjacent to the recessed surface providing connection between the opening and the window.

32. The implant of claim 22, wherein the anterior wall and the posterior wall each comprises a middle portion, a first side portion merges into the right lateral wall and a second side portion merges into the left lateral wall, wherein the first and the second portions are curved with equal radius and the middle portion is straight or less curved compared to the two side portions.

33. The implant of claim 22, wherein the recess is formed having as a diamond shaped hexagon proximate to a center of the center of the anterior wall,
wherein the implant further comprises at least one second diamond shaped hexagon interface on the left lateral wall or right lateral wall and formed at 45 degree angle from the center of the anterior wall.

34. The implant of claim 22, further comprising:
a superior groove provided on the superior surface sized and configured to receive an insertion tool, the superior groove extending at least partially between the anterior and posterior walls; and
an inferior groove provided on the inferior surface sized and configured to receive an insertion tool, the inferior groove extending at least partially between the anterior and posterior walls.

35. A spinal implant for insertion between adjacent upper and lower vertebral endplates, the spinal implant comprising:
superior and inferior surfaces for contacting the upper and lower endplates respectively with each surface comprising a plurality of surface teeth;
a side wall connecting the superior and inferior surfaces, wherein the side wall comprises an anterior wall and a posterior wall that are connected by a right lateral wall and a left lateral wall, wherein the posterior wall is shorter than the anterior wall such that an angulation between the superior and the inferior surfaces is from about 2 to about 30 degrees;
vertical through-channels extending through the implant from the superior surface to the inferior surface with at least one vertical strut separating the channels, the vertical strut including a window providing a connection between the two through-channels;
at least one opening and adjacent recessed surface formed in the anterior wall, the opening being adapted to receive an insertion tool; and
a channel formed adjacent to recessed surface providing connection between the opening and the window,
wherein a width of the implant is defined as a longitudinal distance between the centers of the right and left lateral walls, a length of the implant is defined as a horizontal distance between the centers of the anterior and posterior walls, and a height of the implant is defined as a vertical distance between the superior and inferior surfaces at an anterior most edge of the implant, the height accounting for a convexity of the superior and inferior surfaces and including one-half of a height of the surface teeth disposed on the superior and inferior surfaces, and
wherein the superior and inferior surfaces are convex having respective radius of curvature values, such that the superior and inferior surfaces have different angulation.

* * * * *